United States Patent [19]
Fridovich et al.

[11] Patent Number: 6,103,714
[45] Date of Patent: *Aug. 15, 2000

[54] OXIDOREDUCTASE ACTIVITY OF MANGANIC PORPHYRINS

[75] Inventors: Irwin Fridovich; Stefan I. Liochev, both of Durham, N.C.

[73] Assignee: Duke University, Durham, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/685,529

[22] Filed: Jul. 24, 1996

Related U.S. Application Data

[63] Continuation of application No. 08/309,318, Sep. 20, 1994, abandoned.

[51] Int. Cl.⁷ ................................................. A61K 31/555
[52] U.S. Cl. ................................................. 514/185
[58] Field of Search ............................................. 514/185

[56] References Cited

U.S. PATENT DOCUMENTS

| | | |
|---|---|---|
| 4,614,723 | 9/1986 | Schmidt . |
| 4,746,735 | 5/1988 | Kruper, Jr. et al. . |
| 4,758,422 | 7/1988 | Quay . |
| 4,837,221 | 6/1989 | Bonnett . |
| 4,851,403 | 7/1989 | Picker et al. . |
| 4,892,941 | 1/1990 | Dolphin et al. . |
| 4,895,719 | 1/1990 | Radhakrishnam . |
| 4,963,367 | 10/1990 | Ecanow . |
| 5,051,337 | 9/1991 | Sakoda et al. . |
| 5,130,245 | 7/1992 | Marklund et al. . |
| 5,162,519 | 11/1992 | Bonnett . |
| 5,169,630 | 12/1992 | Okaya et al. . |
| 5,171,680 | 12/1992 | Mullenbach et al. . |
| 5,202,317 | 4/1993 | Bruice . |
| 5,217,966 | 6/1993 | Bruice . |
| 5,223,538 | 6/1993 | Fridovich . |
| 5,227,405 | 7/1993 | Fridovich . |
| 5,236,914 | 8/1993 | Meunier . |
| 5,236,915 | 8/1993 | Fiel . |
| 5,248,603 | 9/1993 | Marklund et al. . |
| 5,262,532 | 11/1993 | Tweedle et al. . |
| 5,284,647 | 2/1994 | Niedballa . |
| 5,366,729 | 11/1994 | Marklund et al. . |
| 5,472,691 | 12/1995 | Marklund et al. . |
| 5,493,017 | 2/1996 | Therien et al. . |
| 5,747,026 | 5/1998 | Crapo et al. . |

FOREIGN PATENT DOCUMENTS

| | | |
|---|---|---|
| 0 127 797 | 12/1984 | European Pat. Off. . |
| 0 186 962 | 7/1986 | European Pat. Off. . |
| 0 282 899 | 9/1988 | European Pat. Off. . |
| 0 336 879 | 10/1989 | European Pat. Off. . |
| 0 337 601 | 10/1989 | European Pat. Off. . |
| 0 345 171 | 12/1989 | European Pat. Off. . |
| 0 414 915 A1 | 3/1991 | European Pat. Off. . |
| 0 462 836 | 12/1991 | European Pat. Off. . |
| 0 524 161 A1 | 1/1993 | European Pat. Off. . |
| 0 532 327 | 3/1993 | European Pat. Off. . |
| 2 676 738 | 11/1992 | France . |
| WO 91/04315 | of 1991 | WIPO . |
| 92/07935 | 5/1992 | WIPO . |
| WO 93/02090 | 2/1993 | WIPO . |
| WO 94/04614 | 3/1994 | WIPO . |
| WO 95/10185 | 4/1995 | WIPO . |
| WO 95/31197 | 11/1995 | WIPO . |
| WO 96/09053 | 3/1996 | WIPO . |

OTHER PUBLICATIONS

Sharma et al, "Synthesis of amphiphilic 5–(4–N–alkylpyridiniumyl)–10,15,20–triphenylporphyrins and their aggregational properties in different solvent systmes", Chemical Abstracts, vol. 123, No. 1, Jul. 3, 1995—Abstract No. 9222.

Schneider et al, "Ligand–Porphyrin Complexes: Quantitative Evaluation of Stacking and Ionic Contributions", J. Org. Chem. 7464–7472 (1994).

Giraudeau et al, "Substituent Effects in the Electroreduction of Porphyrins and Metalloporphyrins", J. Am. Chem. Soc. 101(14):3857–3862 (1979).

Inoue et al, "Expression of a Hybrid Cu/Zn–type Superoxide . . . ," J. Bio. Chem., vol. 266, No. 25, pp. 16409–16414 (1991).

Day et al, "Manganic Porphyrins Possess Catalase Activity . . . ," Arch. Biochem. Biophys., vol. 347, No. 2, pp. 256–262 (1997).

Tsan, M–F., "Superoxide Dismutase and Pulmonary Oxygen Toxicity," XP–002074505, pp. 286–290, 1994.

Naruta et al. (1991) J. Am. Chem. Soc. 113:3595–3596.

Leondiadis et al. (1989) J. Org. Chem. 54:6135–6138.

Foran et al, "Effect of Electrolyte Concentration on Axial Anion Ligation in Manganese(III) meso–Tetraphenylporphyrin Chlorides", Inorg. Chem. 31:1463–1470 (1992).

Milgrom, Facile Aerial Oxidation of a Porphyrin. Part 3. Some Metal Complexes of meso–Tetrakis–(3, 5–di–t–butyl–4–hydroxyphenyl)porphyrin, J. Chem. Soc. Perkin Trans. 11:71–79 (1988).

Bockhorst and Hoehn–Berlage, "An Optimized Synthesis of Manganese meso–Tetra(4–sulfonato–phenyl)porphine: A Tumor–Selective MRI Contrast Agent", Tetrahedron 50(29):8657–8660 (1994).

Keinan et al, "Catalytic Antibodies. Circular Dichroism and UV–Vis Studies of Antibody–Metalloporphyrin Interactions", Inorg. Chem. 31:5433–5438 (1992).

Marx, "Role of Gene Defect in Heredity ALS Clarified", Science 261:986 (1993).

Epp et al, "Superoxide Dismutase Activity of Manganese Chelates", 76–78 (1986).

Bors et al, "An expanded function for superoxide dismutase", Chemical Abstracts 115:388 (1991), Abstract No. 109185h.

Milgrom et al, "Redox Behaviour of Phenolic Porphyrins in Basic Solutions: A Reappraisal", Free Rad. Res. 24(1):19–29 (1996).

(List continued on next page.)

Primary Examiner—Keith D. MacMillan
Attorney, Agent, or Firm—Nixon & Vanderhye P.C.

[57] ABSTRACT

The present invention relates, in general, to porphyrin complexes and, in particular, to methods of using porphyrin complexes to impart oxidoreductase activity.

19 Claims, 11 Drawing Sheets

OTHER PUBLICATIONS

Szabo et al, "Evaluation of the relative contriubtion of nitric oxide and peroxynitrate to the suppression of mitochondrial respiration in immunostimulated macrophages using a manganese mesoporphyrin superoxide dismutase mimetic and peroxynitrite scavenger", FEBS Letters 381:82–86 (1996).

Patel et al, "Requirement for Superoxide in Excitotoxic Cell Death", Neuron 16:345–355 (1996).

Bamford et al, "The Squalestatins: Synthesis and Biological Activity of Some C3–Modified Analogues; Replacement of a Carboxylic Acid or Methyl Ester with an Isoelectric Heterocyclic Functionality", J. Med. Chem. 38:3502–3513 (1995).

Szabo et al, "Peroxynitrite is Involved in the Pathogenesis of the Vascular Contractile and Energetic Failure in Endotoxic Shock", Shock Society Meeting (1996).

Stralin et al, "Effects of Oxidative Stress on Expression of Extracellular Superoxide Dismutase. CuZn–Superoxide Fibrobast", Biochem. J. 298:347–352 (1994).

Folz et al, "Extracellular Superoxide Dismutase (SOD3): Tissue–Specific Expression, Genomic Characterization, and Computer–Assisted Sequence Analysis of the Human EC SOD Gene", Genomics 22:162–171 (1994).

Clyde et al, "Distribution of Manganese Superoxide Dismutase mRNA in Normal and Hyperoxic Rat Lung", American Journal of Respiratory Cell and Molecular Biology 8:530–537 (1993).

Wolberg et al, Electrical and Electron Paramagnetic Resonance Studies of Metalloporphyrins and Thier Electrochemical Oxidation Products: Journal of the American Chemical Society 92(10):2982–2990 (1970).

Pasternack et al, "Superoxide Dismutase Activities of an Iron Porphyrin and Other Iron Complexes", Journal of the American Chemical Society 101(4):1026–1031 (1979).

Winkelman, James, "The Distribution of Tetraphenylporphinesulfonate in the Tumor–bearing Rat", Cancer Research 22:589–596 (1962).

Moisy et al. "Catalytic Oxidation of 2.6–Di–Terbutylphenol by Molecular Oxygen Electroassisted by Poly(Pyrrole–Manganese–Porphyrin)", New J. Chem. 13:511–514 (1989).

Malinski et al, "Characterization of Conductive Polymeric Nickel(II) Tetrakis(3–methoxy–4–hydroxy–phenyl)Porphyrin as an Anodic Material for Electrocatalysis", J. Electrochem. Soc. 138(7):2008–2015 (1991).

Weinraub et al, "Chemical properties of water–soluble porphyrins. 5. Reactions of some manganese (III) porphyrins with the superoxide and other reducing radicals", Int. J. Radiat. Biol. 50(4):649–658 (1986) (Abs).

Fajer et al, "n–Cation Radicals and Dications of Metalloporphyrins", Journal of the American Chemical Society 92(11):3451–3459 (1970).

Pasternack et al, "Aggregation of Nickel(II), Coopwer (II), and Zinc(II) Derivatives of Water–Soluble Porphyrins", Inorganic Chemistry 12(11):2606–2610 (1973).

Datta–Gupta et al, "Synthetic Porphyrins. I. Synthesis and Spectra of Some para–Substituted meso–Tetraphenylporphines (1)", J. Heterocycl. Chem. 3:495–502 (1966).

Harriman et al, "Photochemistry of Manganese Porphyrins Part 2.—Photoreduction", pp. 1543–1552, 1994.

Longo et al, "The Synthesis and Some Physical Properties of ms–Tetra(pentafluorophenyl)–porphin and ms–Tetraphenylporphines (1)", Notes 6:927–931 (1969).

Barnitz McLauglin et al, "Reactions of Fe [11] (meso–α,α,α, α–tetrakis(O–(N–methylisonicotinami-co)phenylporphyrin)$^{5-}$ and Fe [11] (mesc–tetrakis(N–methylpyridinium–4–hy porphyrin)$^{3-}$ with Nc$^-$ $CO_2$-$CO_2$-, and $O_2$-", Inorg. Chem. 32:941–947 (1993).

Pasternack et al, "On the Aggregation of Mesc–Substituted Water–Soluble Porphyrins", Journal of American Chemical Society 94(13):4511–4517 (1972).

Datta–Gupta et al, "Synthetic Porphyrins II Precaration and Spectra of Some Metal Chelates of para[11], Journal of Substituted–mesa–Tetraphenylporphines", Journal of Pharmaceutical Science 57 2):300–304 1968).

Boissinot et al, "Rational Design and Expression of a Heparin–Targeted Human Superoxide Dismutase", Biochemical and Biophysical Research Communication 190(1):250–256 (1993).

Oury et al, "Cold–induced Brain Edema in Mice", The Journal of Biological Chemistry 268(21):15394–15398 (1993).

Oury et al, "Extracellular superoxide dismustase, nitric oxide, and central nervous system $O_2$ toxicity", Proc. Natl. Acad. Sci. USA 89:9715–9719 (1992).

Pasternack et al, "Catalyst of the Disproportionation of Superoxide by Metalloporphyrins III", Journal of Inorganic Biochemistry 15:261–267 (1981).

Oury et al, "Establishment of Transgenic Mice Expressing Human Extracellular Superoxide Dismutase", American Review of Respiratory Disease 143(4):A515 (1991), International Conference Supplement Abstracts—No. 236.

Oury et al, "Transgenic Mice Superexpressing Human Extracellular Superoxide Dismutase Show Increased Resistance to Cold–induced Brain Edema, But are More Susceptible to Hyperbaric Oxygen", American Review of Respiratory Disease 145(4):A713 (1992), International Conference Supplement Abstracts—No. 211.

Oury et al, "Immunocytochemical Localization of Extracellular Superoxide Dismutase in Human Lung", American Review of Respiratory Disease 147(4):A713 (1993), International Conference Supplement Abstracts—No. 246.

Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the Graduate School of Duke University (Jun. 17, 1993).

Gosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691–4699 (1995).

De Peretti et al, "Imidozol[2,1–b]benzoxazole–3–acetamide derivatives, their preparation, and their therapeutic use", Chemical Abstracts 121:1016, Abstract No. 121:200896u, 1984.

Oberley et al, "Anticancer activity of metal compounds with superoxide dismutase activity", Agents and Actions 15(5/6):535–538 (1984).

Collman et al, "Synthesis of "Face to Face" Porphyrin Dimers Linked by 5,15–Substituents: Potential Binuclear Multielectron Redox Catalysts", J. Am. Chem. Soc. 103:516–533 (1981).

Gassman et al, "Electronic Effects of Peripheral Substituents in Porphyrins: X–ray Photoelectron Spectroscopy and ab Initio Self–Consistent Field Calculations", J. Am. Chem. Soc. 114:9990–10000 (1992).

Bishop et al, "The Reaction of Thiomides with Phosphorus Ylides", J. Org. Chem. 56:5079–5091 (1991).

Picker et al, "Cobalt(III) complexes of water soluble synthetic meso–substituted porphyrins as radiation sensitizers for oxic and hypoxic tumor cells", 8–Radiation 112:405 (1990) Abstract No. 112:73026d.

McCord et al, "Superoxide Dismutase—An Enzymic Function for Erythrocuprein", Biochemistry 492, p. 346, 1984.

McCord et al, Superoxide Dismutase An Enzymic Function for Erythrocuprein (Hemocuprein), The Journal of Biological Chemistry 244(22):6049–6055 (1969).

Crapo et al, "Superoxide Dismutase and Oxygen Toxicity", Clincal Research, p. 222, 1995.

Crapo et al, "The Failure of Aerosclized Superoxide Dismutase to Modify Pulmonary Oxygen Toxicity", American Review of Respiratory Disease 115:1027–1033 (1977).

Joester et al, "Superoxide Dismutase Activity of $Cu^{2+}$–Amino Acid Chelates", FEBS Letters 25(1):25–28 (1972).

Brigelius et al, "Superoxide Dismutase Activity of Low Molecular Weight Cu2+–Chelates Studied by Pulse Radiolysis", FEBS Letters 47(1):72–75 (1974).

Sorenson, John R.J., "Copper Chelates as Possible Active Forms of the Antiarthritic Agents", Journal of Medicinal Chemistry 19(1):135–148 (1976).

deAlvare et al, "Mechanism of Superoxide Anion Scavenging Reaction by Bis–(Salicylato)–Copper(II) Complex", Biochemical and Biophysical Research Communications 69(3):687–694 (1976).

Halliwell, Barry, "The Superoxide Dismutase Activity of Iron Complexes", FEBS Letters 56(1):34–38 (1975).

McClune et al, "Catalysis of Superoxide Dismutation by Iron–Ethylenediaminetetraacetic Acid Complexes. Mechanism of the Reaction and Evidence for the Direct Formation of an Iron(III)–Ethylenediaminetetraacetic Acid Peroxo Complex from the Reaction of Superoxide with Iron(II)–Ethylenediaminetetraacetic Acid", Communications to the Editor, pp. 5220–5222 (1977).

Diguiseppi et al, "Putative Superoxide Dismutase Activity of Iron–EDTA: A Reexamination", Archives of Biochemistry and Biophysics 203(1):145–150 (1980).

Robertson, Jr. Et al, "Does Copper–D–Penicillamine Catalyze the Dismutation of $O_2^-$?", Archives of Biochemistry and Biophysics 203(2):830–831 (1980).

Werringloer et al, "The Integration of Divalent Copper and the Microsomal Electron Transport System", The Journal of Biological Chemistry, 254(23):11839–11846 (1979).

Pasternack et al, "Catalyst of the Disproportionation of Superoxide by Metalloporphyrins", Journal of Inorganic Biochemistry 11:261–267 (1979).

Archibald et al, Manganese and Defenses against Oxygen Toxicity in *Lactobacillus plantarum*, Journal of Bacteriology 145(1):442–451 (1981).

Archibald et al, Manganese, Superoxide Dismutase, Oxygen Tolerance in Some Lactic Acid Bacteria, Journal of Bacterilogy 146(3):928–936 (1981).

Archibald et al, The Scavenging of Superoxide Radical by Manganous Complex: In Vitro, Archives of Biochemistry and Biophysics 214(2):452–463 (1982).

Archibald et al, Investigations of the State of the Manganese in *Lactobacillus plantarum*, Archives of Biochemistry and Biophysics 215(2):589–596 (1982).

Darr et al, "A Mimic of Superoxide Dismutase Activity Based Upon Desferrioxamine B and Manganese(IV)", Archives of Biochemistry and Biophysics 258(2):351–355 (1987).

Beyer, Jr., Characterization of a Superoxide Dismutase Mimic Prepared from Desferrioxamine and $MnO_2$, Archives of Biochemistry and Biophysics 271(1):149–156 (1989).

Faulkner et al, "Characterization of Mn(III) Complexes of Linear and Cyclic Desferrioxamines as Mimics of Superoxide Dismutase Activity", Archives of Biochemistry and Biophysics 310(2):341–346 (1994).

Faulkner et al, Stable Mn(III) Porphyrins Mimic Superoxide Dismutase in Vitro and Substitute for It in Vivo, The Journal of Biological Chemistry 269(38):23471–23476 (1994).

Liochev et al, "A Cationic Manganic Porphyrin Inhibits Uptake of Paraquat by *Escherichia coli*", Archives of Biochemistry and Biophysics 321(1):271–275 (1995).

Peretz et al, "Chemical properties of water–soluble porphyrins 3. The reaction of superoxide radicals with some matailoporphyrins", Int. J. Radiat. Biol. 42(4):449–456 (1982).

Baudry et al, "Salen–Manganese Complexes are Superoxide Dismutase–Mimics", Biochemical and Biophysical Research Communication 192(2):964–968 (1993).

Gonzalez et al, "EUK–8, a Synthetic Superoxide Dismutase and Catalase Mimetic, Ameliorates Acute Lung Injury in Endotexemic Swine", The Journal of Pharmacology and Experimental Therapeutics 275(2):798–806 (1995).

Deune et al, "Prevention of Ischemia–Reperfusion Injury with a Synthetic Metalloprotein Superoxide Dismutase Mimic. SC52608", Plastic and Reconstructive Surgery 98(4):711–718 (1996).

Lowe et al, "Comparison of the cardiovascular effects of two novel superoxide dismutase mimetics, SC–55858 and SC–54417, in conscious dogs", European Journal of Pharmacoloty 304:81–86 (1996).

Weiss et al, "Manganese–based Superoxide Dismutase Mimetics Inhjibit Neutral Infiltration in Vivo", The Journal of Biological Chemistry 271(42):26149–26156 (1996).

Jin et al, "A new route to water soluble porphyrins: phosphonium and ammonium type cationic porphyrins and self–assembly", Chem. Commun., pp. 1939–1940 (1996).

Pitié et al, "Oxidation at Carbon–1 of DNA Deoxyriboses by the Mn–TMPyP/KHSO5 System Results from a Cytochrome P–450–Type Hydroxylation Reaction", J. Am. Chem. Soc. 117:2935–2936 (1995).

Libby et al, "Cationic Porphyrin Derivatives As Inhibitors of Polyamine Catabolism", Biochemical Pharmacology 50(9):1527–1530 (1995).

Ilan et al, "Superoxide Dismuting Activity of an Iron Porphyrin", Inorg. Nucl. Chem. Letters 17(3/4):93–96 (1981).

Solomon et al, "Chemical properties of Water–Soluble Porphyrins. 2. The Reaction of Iron(III) Tetrakis(4–N–methylpyridyl)porphyrin with the Superoxide Radical Dioxygen Couple", J. Phys. Chem. 86:1842–1849 (1982).

Weinraub et al, "Chemical Properties of Water–Soluble Porphyrins. 1. Equilibria between Some Ligands and Iron(III) Tetrakis (4–N–methylpyridyl)porphyrin", J. Phys. Chem. 86:1839–1842 (1982).

Day et al, "A Metalloporphyrin Superoxide Dismutase Mimetic Protects Against Paraquat–Induced Endothelial Cell Injury, in Vitro", The Journal of Pharmacology and Experimental Therapeutics 275(3):1227–1232 (1995).

Kariya et al, "Superoxide Dismutase (SOD) Activity with Fe–chlorin e6–Na and Suppression of Malignant Tumor Growth in Rats", Cancer Biotherapy 10(2):139–145 (1995).

Liochev et al, A Cationic Manganic Porphyrin Inhibits Uptake of Paraquat by *Escherichia coli*, Archives of Biochemistry and Biophysics 321(1):271–275 (1995).

Ohkawa et al, "Assay for Lipid Peroxides in Animal Tissues by Thiobarbituric Acid Reaction", Analytical Biochemistry 95:351 (1979).

Yue et al, "Carvidilol, a New Vasodilator and Beta Adrenoceptor Antagonist, is an Antioxidant and Free Radical Scavenger", The Journal of Pharmacology and Experimental Therapeutics 263:(1992).

Song et al, "Anti–HIV activities of anionic metalloporphyrins and related compounds", Antiviral Chemistry and Chemotherapy 8(2):85 (1996).

Harriman and Porter, "Photochemistry of Manganese Porphyrins", J. Chem. Soc. 275:1532–1542 (1979).

Bedioui et al, "Metalloporphyrin–Polypyrrole Film Electrode: Characterization and Catalytic Application", J. Electroanal. Chem. 207:87–99 (1986).

Ruoslahti et al, "Arg–Gly–Asp: A Versatile Cell Recognition Signal", Cell 4:517–518 (1986).

Kumar et al, "Radioprotection by Antioxidant Enzymes and Enzyme Mimetics", Pharmac. Ther. 39:301–309 (1988).

Weiss et al, "Evaluation of Activity of Putative Superoxide Dismutase Mimics", The Journal of Biological Chemistry 2638(31):23049–23054 (1993).

Parge et al, "Atomic structures of wild–type and thermostable mutant recombinant human Cu,Zn superoxide dismutase", Proc. Natl. Acad. Sci. USA 89:6109–6113 (1992).

Lappin, "Part III Bioinorganic Studies", Inorganic Reaction Mechanisms 7:334–343 (1981).

Schezer et al Reactivity of Porphyrin Germonresion Angew Chem. 57:380 (1975).

Mn(III) tetra(4-pyridyl)porphyrin
MnTPyP

Mn(III) tetrakis(1-methyl-4-pyridyl)porphyrin
MnTMPyP

Mn(III) tetrakis(trimethylammonio)phenyl porphyrin
MnTMAP

Mn(III) tetrakis(4-benzoic acid)porphyrin
MnTBAP

Mn(III)α,α,α,β-tetrakis(1-methylisonicotinamido)
phenyl]porphyrin
MnTMINP

6,103,714

OXIDOREDUCTASE ACTIVITY OF MANGANIC PORPHYRINS

This is a continuation of Ser. No. 08/309,318, filed Sep. 20, 1994, abandoned.

TECHNICAL FIELD

The present invention relates, in general, to porphyrin complexes and, in particular, to methods of using porphyrin complexes to impart oxidoreductase activity.

BACKGROUND

Superoxide radical ($O_2^-$), generated during both spontaneous and enzyme-catalyzed oxidations, is catalytically scavenged by superoxide dismutases (SODs); which, by so doing, provide an important defense (Beyer et al, Prog. Nucl. Acids Res. 40:221 (1991), Fridovich, J. Biol. Chem. 264:7761 (1989)). $O_2^-$, if not removed by SOD, can: initiate free radical chain oxidations of low molecular weight reductants (Nishikimi, Arch. Biochem. Biophys. 166:273 (1975), Ballou et al, Biochem. Biophys. Res. Commun. 36:898 (1969), Fridovich et al, J. Biol. Chem. 233:1578 (1958), McCord et al, J. Biol. Chem. 243:5753 (1968), McCord et al, J. Biol. Chem. 244:6056 (1969), McCord et al, J. Biol. Chem. 244:6049 (1969)); inactivate enzymes (Kuo et al, J. Biol. Chem. 262:4724 (1987), Takabatake et al, Chem. Pharm. Bull. 40:1644 (1992), Smyk-Randall et al, Free Rad. Biol. Med. 14:609 (1993), Gardner et al, J. Biol. Chem. 266:1478 (1991), Gardner et al, J. Biol. Chem. 266:1478 (1991), Gardner et al, J. Biol. Chem. 266:19328 (1991), Flint et al, J. Biol. Chem. 268:22369 (1993)); and can give rise to very reactive hydroxyl or alkoxyl radicals through iron- or copper-, catalyzed interactions with HOOH or ROOH (Sutton et al, Free Rad. Biol. Med. 6:53 (1989), Smith et al, Free Rad. Res. Commun. 8:101 (1990), Nakae et al, Arch. Biochem. Biophys. 279:315 (1990), Tushelasvili et al, J. Biol. Chem. 266:6401 (1991), Mello-Filho et al, Mutat. Res. 251:109 (1991), Halliwell et al, FEBS Lett. 307:109 (1992)). $O_2^-$ can also react, at a diffusion-limited rate, with NO; yielding peroxynitrite (Huie et al, Free Rad. Res. Commun. 18:195 (1993)).

It is reasonable, therefore, that $O_2^-$ should be a participant in a variety of physiological and pathological processes. The ability of SOD to ameliorate reperfusion injury (Concannon et al, Microsurgery 12:18 (1991), Triana et al, Circ. Res. 69:731 (1991), Erlansson et al, Free Rad. Biol. Med. 9:59 (1990), Fujita et al, Biochem. Biophys. Res. Commun. 129:191 (1992), Hatori et al, Free Rad. Biol. Med. 13:137)), inflammations (Ward et al, Free Rad. Biol. Med. 5:403 (1988), Parizada et al, Free Rad. Res. Commun. 15:297 (1991), Oyanagui et al, Biochem. Pharmacol. 42:991 (1991)), multiorgan failure (Marzi et al, J. Trauma 35:110 (1993)), brain trauma (Muizeloar, Ann. Emerg. Med. 22:1014 (1993)), and other conditions (Flohé, Mol. Cell. Biochem. 84:123 (1988), Gorecki et al, Free Rad. Res. Commun. 12–13:401–410 (1991)), indicates that this is the case. It is apparent therefore that mimics of SOD activity are useful pharmaceutical agents. The ideal mimic should be active, stable, and specific for its substrate ($O_2^-$). A number of metal complexes have been reported to catalyze the disputation of $O_2^-$ (see, for example, McLaughlin et al, Inorg. Chem. 32:941 (1993), Tian et al, Biochem. Biophys. Res. Commun. 191:646 (1993), Kitajima et al, Inorg. Chem. 32:1879 (1993), Baudry et al, Biochem. Biophys. Res. Commun. 192:964 (1993)). Even the best of the compounds described to date, however, exhibit only ~1% of the activity of SOD, are not stable to EDTA, and/or can catalyze reactions in addition to the disputation of $O_2^-$.

SUMMARY OF THE INVENTION

The present invention relates to a method of effecting oxidoreduction in a sample containing $O_2^-$. The method comprises contacting the sample with a metallic porphyrin complex having substituents on the methine carbons under conditions such that the complex is reduced and reoxidized by the $O_2^-$.

Objects and advantages of the present invention will be clear from the description that follows.

DETAILED DESCRIPTION OF THE INVENTION

Figure 1:
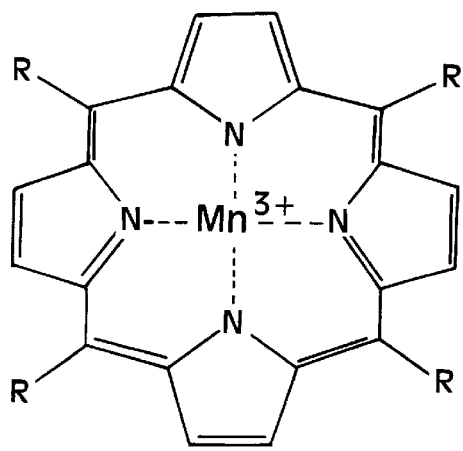
FIG. 1. Mn porphyrins. Shown are the porphyrin structures, names, and abbreviations used herein.
Figure 1:
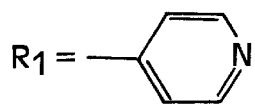
Figure 1:
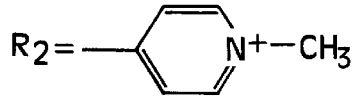
Figure 1:
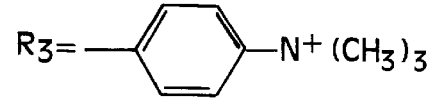
Figure 1:
Figure 1:
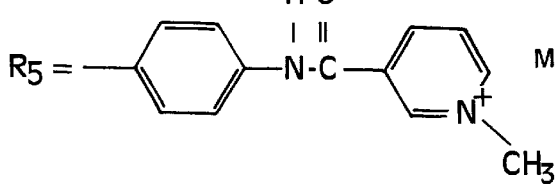

Manganese porphyrins are well characterized and stable (Collman et al, Science 261:1404 (1993), Tsang et al, Inorg. Chem. 29:2848 (1990), Harriman et al, J. Chem. Soc. Faraday Trans. 275:1532 (1979)). Moreover, such compounds have been reported to catalyze the dismutation of $O_2^-$ with rate constants as high as $4 \times 10^7$ $M^{-1}$ $s^{-1}$ (Farragi, M. in Oxygen Radicals in Chemistry and Biology (Bors, W., Saran, M., and Tait, D., eds.) pp. 419–430, Walter de Gruyter, Publ., Berlin (1984), Pasternak et al, J. Inorg. Biochem. 15:261 (1981)). The present invention results from the discovery that manganic porphyrins exhibit reversible redox behavoir. More specifically, the invention results from the finding that Mn(III) 5, 10, 15, 20-tetrakis(1-methyl-4-pyridyl)-21H,23H-porphine tetra-p-tosylate (MnTMPyP) in vivo is reduced enzymatically at the expense of NADPH and non-enzymatically by GSH, with a rate constant for reoxidation of the reduced form by $O_2^-$ of $4 \times 10^9$ $M^{-1}s^{-1}$. The compound thus acts as a NADPH/GSH:$O_2^-$ oxidoreductase in vivo. Such action requires replenishment of NADPH and GSH; that can be achieved at the expense of carbon source (eg glucose).

MnTMPyP is not the only manganic porphyrin that imparts an NADPH:$O_2^-$ oxioreductase activity and acts like a GSH:$O_2^-$ oxidoreductase. Several manganic porphyrins, with substituents on the methine carbons, were prepared and examined for stability, redox behavior, catalysis of the dismutation of superoxide radical ($O_2^-$), and for the ability to protect a SOD-null strain of *E. coli* against dissolved oxygen, and a SOD-competent strain against paraquat (see Example that follows). All of the compounds tested exhibited reversible redox behavoir and were stable to EDTA in both the oxidized and reduced states, and several were able to catalyze the dismutation of $O_2^-$ with rate constants of ~$10^7$ $M^{-1}s^{-1}$. The marked protective effects of certain of these compounds exceeded that which could be anticipated on the basis of such rate constants.

While the present invention is described with reference to manganic porphyrins bearing substituents on the methine bridge carbons, other metals can also be used. Examples of such metals include iron (Fe(III)→Fe(II)), cobalt (Co(III)→Co(II)), nickle (Ni(II)→Ni(I)) and copper (Cu(II)→Cu(I)). The complexes of the present invention can be obtained commercially or can be prepared using methods known in the art (see also Example that follows).

The oxidoreductase function of the molecules (complexes) of the invention permits their administration as pharmaceuticals in concentrations sufficiently low to avoid problems associated with toxicity, which concentrations are sufficiently high to achieve the effect sought. Appropriate doses can be readily determined by one skilled in the art, given the present disclosure (as an example, a dose of 1–50 mg/kg can be used). As regards the formulation of the molecules of the invention as compositions and as regards methods of using the molecules of the invention (eg in autoxidation inhibition and in protection), see application Ser. No. 08/089,813 (the entire contents of which is incorporated herein by reference) (see also U.S. Pat. No. 5,223,538 and U.S. Pat. No. 5,227,405).

The invention is illustrated by way of reference to the non-limiting Example that follows.

EXAMPLE

Porphyrin Mimetics Substitute for SOD In Vivo

Preparation of Mn Porphyrins—Complexes of $H_2$-TMPyP and $H_2$-TMAP, with Mn, Fe or Co, were prepared by the method of Pasternack et al, Biochemistry 22:2406 (1983). Metal ligation was followed spectrophotometrically. The MnTMPyP complex was characterized in terms of its Soret band at 463 nm, $E_m = 9.2 \times 10^4$ $M^{-1}$ $cm^{-1}$ (Harriman et al, J. Chem. Soc. Faraday Trans. 275:1532 (1979); Pasternack et al, Biochemistry 22:2406 (1983)). The Soret band for the MnTMAP complex was at 465 nm with $E_m = 9.2 \times 10^4$ $M^{-1}$ $cm^{-1}$. As judged by constancy of their absorption spectra, these compounds were stable from pH 1–9. Moreover, the Mn-porphyrins did not oligomerize in the range 0–3 μM, since there were no deviations from Beers law. The Mn complexes of $H_2$-TPyP and of $H_2$-TBAP were prepared by the method of Harriman and Porter (J. Chem. Soc. Faraday Trans. 275:1532 (1979)). For MnTPyP the Soret band was at 463 nm and E was $9 \times 10^4$ $M^{-1}$ $cm^{-1}$; while for MnTBAP the corresponding values were 468 nm and $9.3 \times 10^4$ $M^{-1}$ $cm^{-1}$ (Harriman and Porter, J. Chem. Soc. Faraday Trans. 275:1532 (1979)).

Assays—Catalysis of the dismutation of $O_2^-$ was measured by using xanthine oxidase plus xanthine as the source Of $O_2^-$ and ferricytochrome c as the indicating scavenger Of $O_2^-$ (McCord et al, J. Biol. Chem. 244:6049 (1969)). Rates of reduction of cytochrome c were followed at 550 nm with a Beckman model DU-70. Assays were conducted in the absence and in the presence of 0.1 mM EDTA in 50 mM potassium phosphate, pH 7.8 and at 25° C. Rate constants for reaction of the metal porphyrins with $O_2^-$ was based on their competition with cytochrome c for reaction with $O_2^-$, using $k_{O_2^-}$, cyt c=$3.0 \times 10^6$ $M^{-1}s^{-1}$ (Koppenol et al, Israel J. Chem. 24:11 (1984)). Possible interference by inhibition of the xanthine oxidase reaction by the test compounds was examined by following the rate of accumulation of urate at 295 nm in the absence of cytochrome c. The oxidation of NADPH was followed at 340 nm. Anaerobic measurements were made using an anaerobic cuvette (Hodgson et al, Anal. Biochem. 51:470 (1973)) purged with $N_2$ which had been passed over a bed of hot copper foil to remove traces of $O_2$ and which was conducted to the cuvette through copper tubing. $O_2$ uptake was followed polarographically with a Clark electrode. All measurements were at 25° C.

Culture of E. coli—Rates of growth of cultures of E. coli were followed turbidimetrically at 700 nm to minimize interferences from the absorbance of test compounds. Culture media were prepared as described by Maniatis et al, Molecular Cloning, A Laboratory Manual, Cold Spring Harbor Press Cold Spring Harbor, N.Y. Supplemented medium contained 0.2% glucose, 0.2% casamino acids and M9 salts in tap water, pH adjusted to 7.0. Minimal medium contained 0.2% glucose and 0.5 mM each of leucine, threonine, proline, arginine and histidine, plus M9 salts in tap water, pH adjusted to 7.0. In some cases Mn-poor medium was prepared by substituting MOPS for the phosphate present in M9 and by using Chelex-100 to remove contaminating metal cations. Cu(II), Zn(II) and Fe(II) were then added to ~1 mg/L. All media were further supplemented with 30 mg/L of thiamine and of D-pantothenic acid. When added to media, test compounds were filter-sterilized. Extracts of cells grown in M-9 medium supplemented with 0.2% casamino acids were prepared, after washing with 50 mM sodium phosphate at pH 7.3 and resuspension in this buffer, by use of the French Press. The lysate was clarified by centrifugation. LB adjusted to pH 7.0 medium was prepared as described (Maniatis et al, Molecular Cloning, A Laboratory Manual, Cold Spring Harbor Press Cold Spring Harbor, N.Y.). Protein was measured by the method of Lowry et al (J. Biol. Chem. 193:265 (1951)).

Electrochemical Characterization of Test Compounds—Cyclic voltammetry was performed using a PAR Model 175 potentiostat and a PAR Model 173 programmer. The working electrode was a polished Pt button electrode pretreated by sonication in 1 N HCl. An Ag/AgCl electrode (Bioanalytical Systems) served as the reference (−200 mV vs NHE), and a 1 mm diameter Pt wire auxiliary electrode. Cyclic voltammetry was performed in 0.05 M phosphate buffer, pH 7.8, 0.1 M NaCl, 21° C. $E_{1/2}$ values were obtained by taking the average of the $E_{pc}$ and $E_{pa}$ values. Typical scan rates were from 100 to 500 mV/sec. The electrochemistry was performed in Argon purged solution with added $Na_2S_2O_4$ to scavenge trace $O_2$. The added $Na_2S_2O_4$ had no influence on the $E_{1/2}$ values obtained for the Mn porphyrins, but increased the current response at the electrode surface by reducing the competition of Mn(II) porphyrin with electrochemically reduced $O_2$ species. 1-Methyl imidazole was also present in the solution to compete for the axial coordination sites on the Mn porphyrins. The 1-methyl imidazole had no influence on the $E_{1/2}$ values obtained, but decreased the $\Delta E_{pp}$ values ($E_{pa}-E_{pc}$). When 1-methyl imidazole was added, the pH of the solution was adjusted to pH 7.8 using 1 N HCl.

Stability of Mn Porphyrins—The structures, proper names and abbreviated designations for the test compounds are given in FIG. 1. The optical spectra of MnTPyP, MnTMPyP, MnTMAP, MnTBAP and MnTMINP were independent of pH in the range 1.0–9.0. These complexes were unaffected by 0.10 mM EDTA; which represented at least a ten-fold excess of EDTA over the test compounds. At pH 7.8 these complexes could be reduced with dithionite and then reoxidized by $O_2$ without loss and this could be done in the presence of excess EDTA. It follows that both the Mn(II) and the Mn(III) forms of these complexes were stable towards EDTA.

Figure 2:
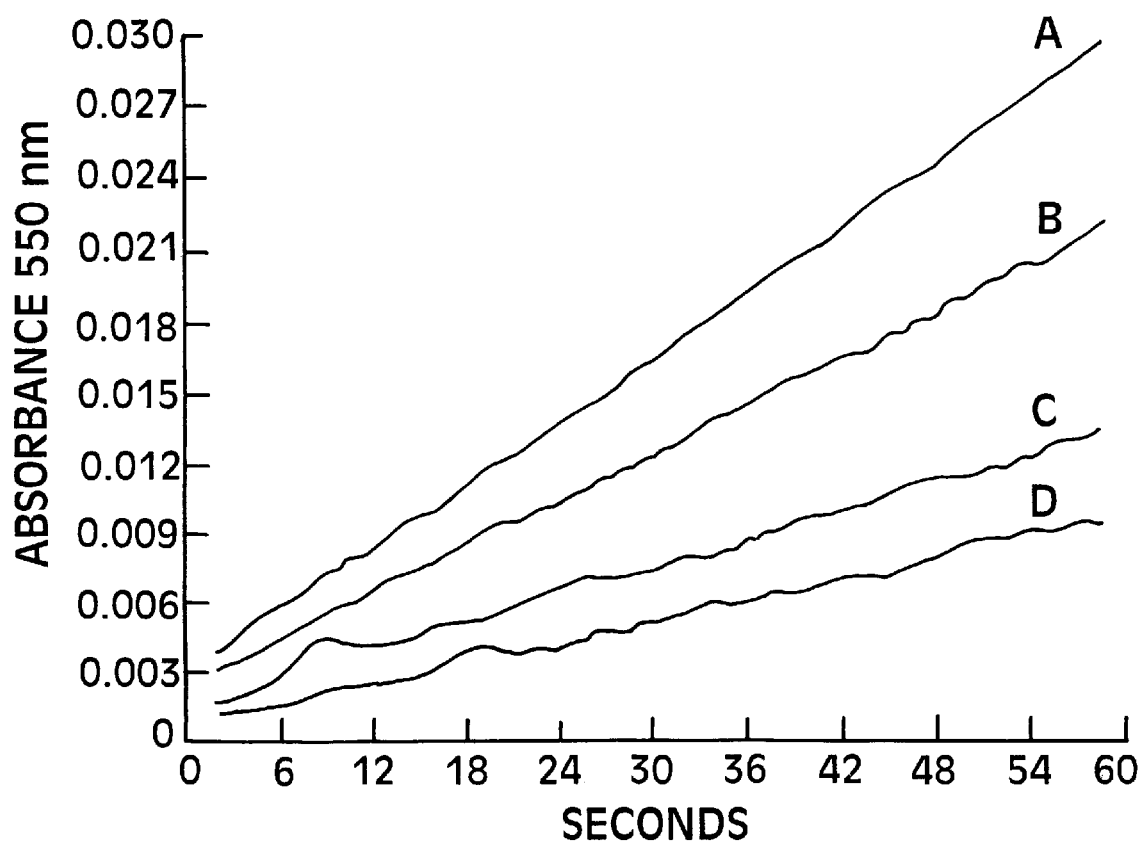
FIG. 2. Reduction of cytochrome $c^{3+}$ in the presence of MnTMPyP. Shown are the absorbance vs. time traces of cyt $c^{3+}$ reduction in the cytochrome $c^{3+}$ assay. Trace A is the reduction of cyt $c^{3+}$ in the absence of MnTMPyP. Trace B) 0.15 μM MnTMPyP, C) 0.75 μM MnTMPyP, and D) 1.15 μM MnTMPyP. Conditions are as follows: 8.9 μM cyt $c^3$, 35 μM xanthine, 3.5 μL of 1 μM xanthine oxidase, 0.05 M phosphate buffer, 0.10 mM EDTA, pH 7.80, 21° C.

Activity in vitro—MnTMPyP exhibited SOD-like activity in the xanthine oxidase-cytochrome c assay, in the presence of a ~100-fold molar excess of EDTA (see FIG. 2). MnTMPyP, tested up to 6 μM, did not inhibit the xanthine oxidase reaction and the optical spectrum of this porphyrin was not changed by exposure to this reaction under the conditions of the assay for SOD activity (McCord et al, J. Biol. Chem. 244:6049 (1969)) but with cytochrome c omitted. These results are in accord with the conclusions of Faraggi (Oxygen Radicals in Chemistry and Biology (Bors, W., Saran, M., and Tait, D. Eds) pp. 419–430, Walter de Gruyter, Publ., Berlin (1984)). Fe(III) TMPyP has previously been noted to react with $H_2O_2$ (Pasternack et al, J. Am. Chem. Soc. 101:1026 (1979)). The Soret band of the Mn(III) TMPyP was similarly diminished by $H_2O_2$ at 1.0 or 10.0 mM. However, when [$H_2O_2$] was only 0.1 mM the bleaching of the Soret band of 12.5 μM Mn(III)TMPyP was very slow; being less than 1% loss of absorbance per minute at 25° C. It follows that attack by $H_2O_2$ would be insignificant in catalase-proficient cells.

Figure 3:
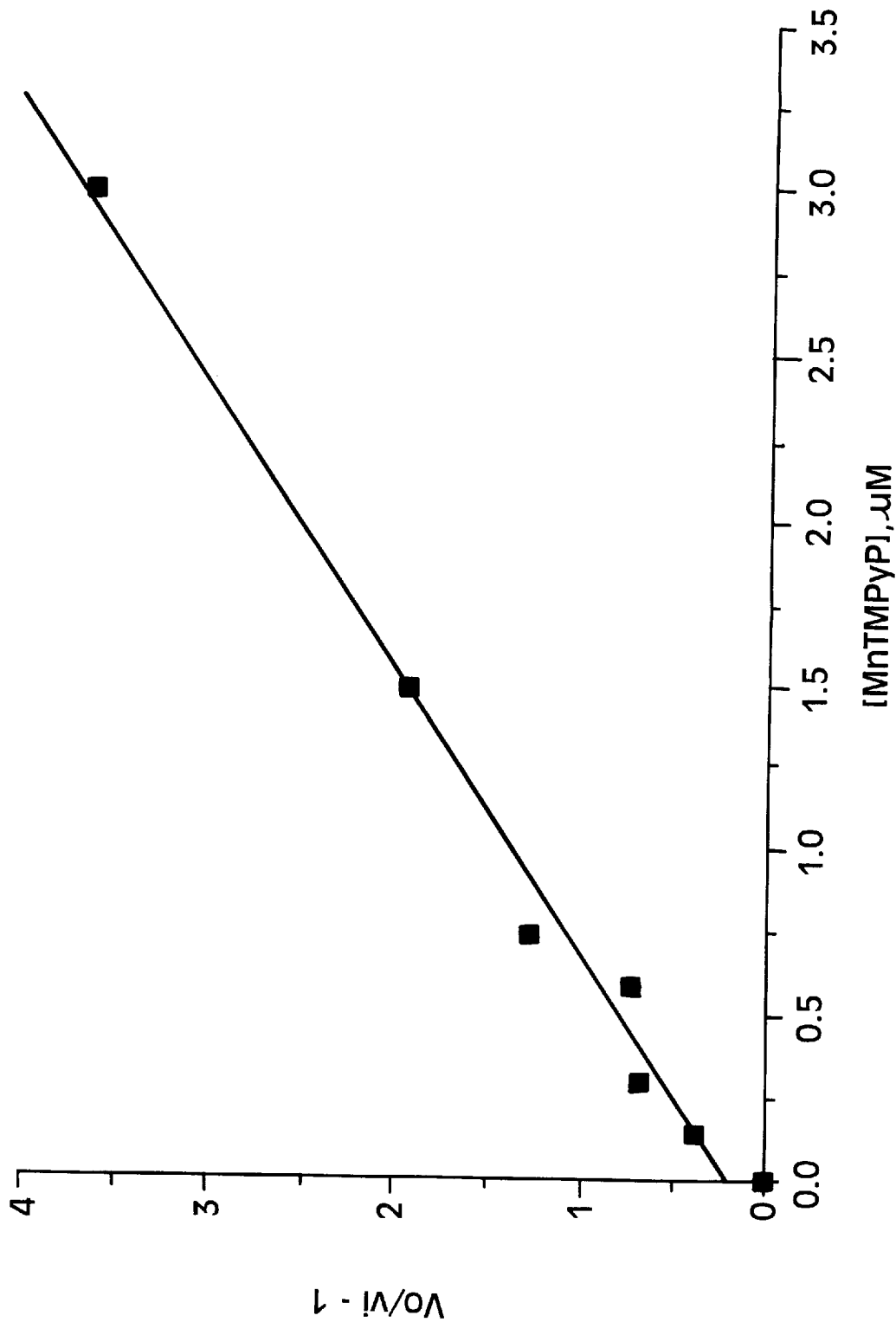
FIG. 3. Asada plot of MnTMPyP SOD activity. The line through the data is the best fit linear regression line ($r^2$= 0.98). Vo=$\Delta AU_{550\,nm}$/min for cyt $c^{3+}$ in the absence of MnTMPyP, and Vi=$\Delta AU_{550\,nm}$/min for $c^{3+}$ reduction in the presence of various concentrations of MnTMPyP, as shown on the x-axis. Conditions are as follows: 8.9 μM cyt $c^{3+}$, 35 μM xanthine, 3.5 μL of 1 AM xanthine oxidase, 0.05 M phosphate buffer, 0.10 mM EDTA, pH 7.80, 21° C.

Inhibition of cytochrome c reduction by MnTMPyP, when plotted according to Sawada and Yamazaki (Biochem. Biophys. Acta 327:257 (1973)), yielded a straight line (FIG. 3) from which $IC_{50}$ was found to be 0.7 (±0.07) μM and from this the rate constant for the reaction of $O_2^-$ with MnTMPyP was found to be $3.9 \times 10^7$ M$^{-1}$s$^{-1}$ at pH 7.8. This agrees very well with the rate constant of $4.0 \times 10^7$ M$^{-1}$s$^{-1}$ determined by Faraggi (Oxygen Radicals in Chemistry and Biology (Bors, W., Saran, M., and Tait, D. Eds) pp. 419–430, Walter de Gruyter, Publ., Berlin (1984)), at pH 8.0, through pulse radiolysis. It appears that Mn(III)TMPyP acts as a SOD-mimic, under the conditions of the SOD assay, without causing detectable side reactions. Comparable data for all of the Mn-porphyrins examined is presented in Table I. It should also be noted that MnTMPyP was apparently unaffected by the $H_2O_2$ which accumulates during the xanthine oxidase reaction since its catalytic activity was not affected by 450 units/ml of catalase.

TABLE I

Results of the Cyclic Voltammetry and the Cytochrome c Assays of the Mn Porphyrins

| Mn Porphyrin | Charge (pH 7.8) | E½(mV, NHE)[a] | $IC_{50}$ (μM)[b] | $k_{cat}$ (M$^{-1}$s$^{-1}$)[b] |
|---|---|---|---|---|
| MnTMPyP | +5 | +60 | 0.70 | $3.9 \times 10^7$ |
| MnTPyP | +1 | 0 | c | c |
| MnTMAP | +5 | −100 | 21 | $1.6 \times 10^6$ |
| MnTMINP | +5 | +44 | c | c |
| MnTBAP | −3 | +110 | d | d | a) Conditions: 0.05 M phosphate buffer, 0.10 M NaCl pH 7.7–7.8, 0.4 to 1.0 mM Mn porphyrin, 0.5–1 equivalent of $Na_2S_2O_4$, 2m M 1-methyl imidazole. Reproducibillty of E½=±10 mV.
b) Conditions: 0.05 M phosphate buffer, 0.10 mM EDTA, pH 7.8, 40 μM xanthine, ca 10 μM cyt $c^{3+}$. Reproducibility of $IC_{50}$ = ±10%.
c) These Mn porphyrins were not active in our assay conditions.
d) MnTBAP interfered with the production of urate, in the presence and absence of 0.1 mM EDTA.

Electrochemical Behavior—Cyclic voltammetry indicated reversible redox behavior for all of the Mn-porphyrins examined; as evidenced by $\Delta E_{pp} \leq 100$ mV at scan rates in the range 100–500 mv/sec. Moreover, in the absence of $O_2$, peak currents for the cathodic and anodic waves were equivalent, also indicative of reversibility. The results of cyclic voltammetry are given in Table 1. $E_{1/2}$ for MnTMPyP is in agreement with Faraggi (Oxygen Radicals in Chemistry and Biology (Bors, W., Saran, M., and Tait, D. Eds) pp. 419–430, Walter de Gruyter, Publ., Berlin (1984)); whereas the value for MnTMAP obtained is 30 mV negative of the previously reported value. Sodium dithionite, which was used to remove traces of $O_2$, and thus to eliminate interferences from the cathodic reduction of $O_2$, did not itself interfere in the potential region used during these measurements.

Figure 4:
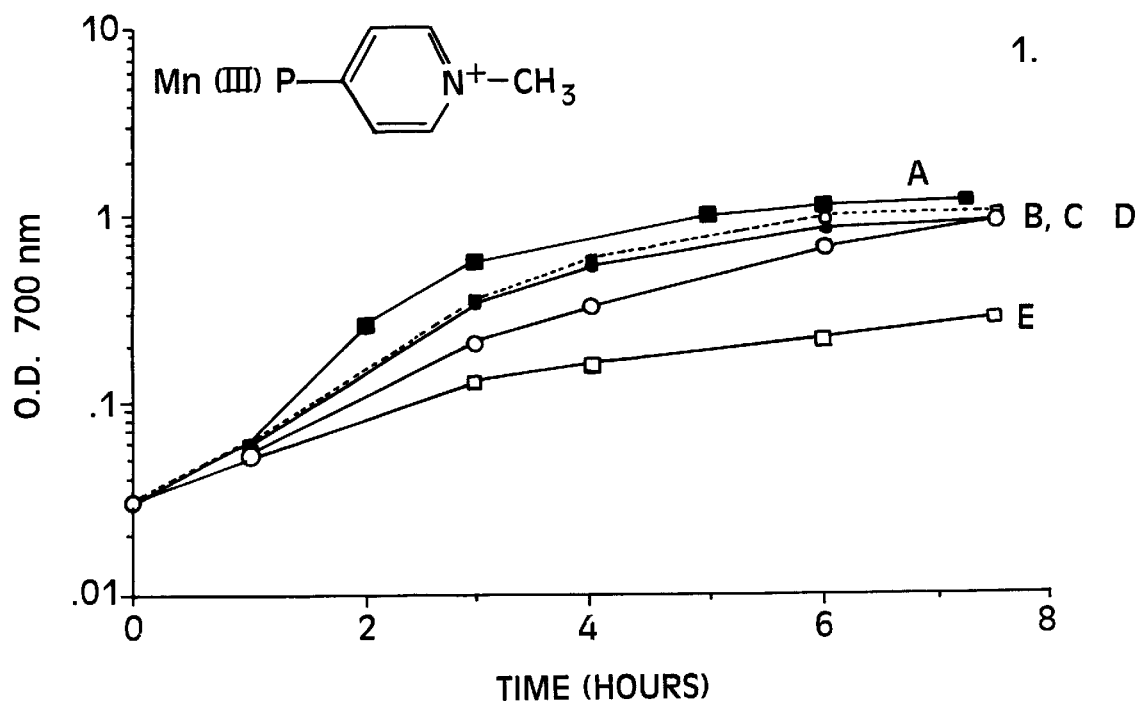
FIG. 4. Growth induction of sodAsodB E. coli mutant with MnTMPyP and MnTBAP. This figure shows the growth curves of E. coli AB1157, and JI1132 in the presence and absence of MnTMPyP and MnTBAP. The traces are as follows: 1. A) AB1157, B, C, D) JI132 in the presence of 21, 51, 100 μM MnTMPyP, respectively, and E) JI132. 2. μl) AB1157, B', C', D') JI132 in the presence of 37, 54, 86 μM MnTBAP, respectively, and E') JI132. Conditions are as follows: M9 salts, phosphate buffer in tap water, 2% casamino acids, 0.2% glucose, 37° C.
Figure 4:
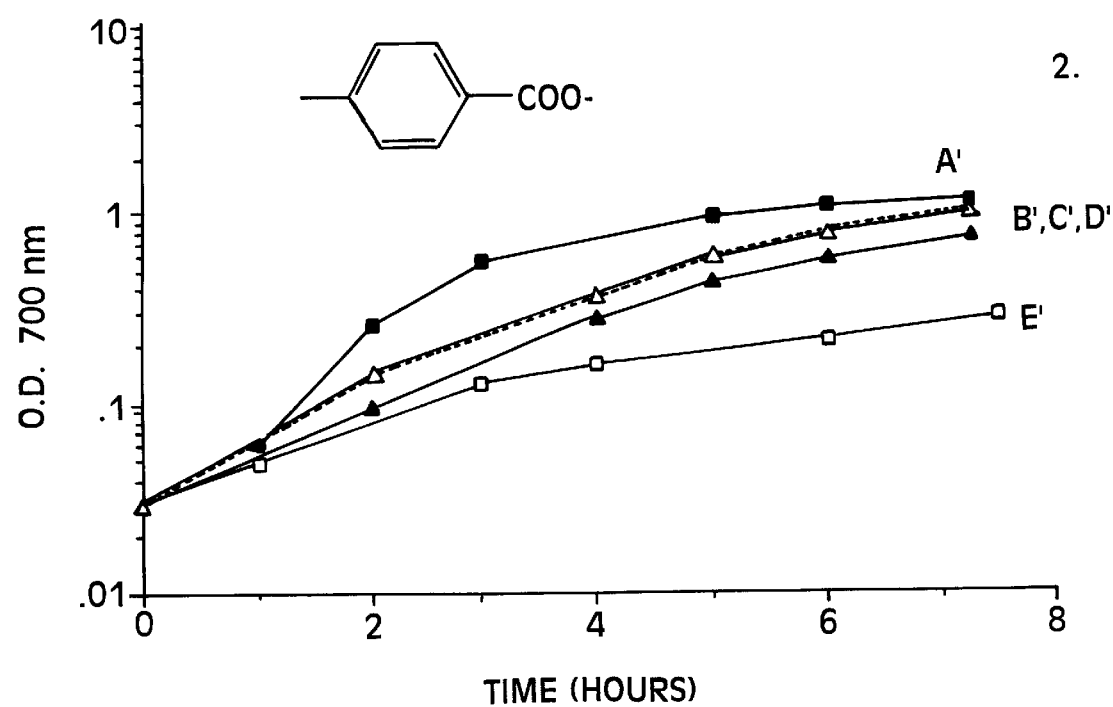
Figure 5:
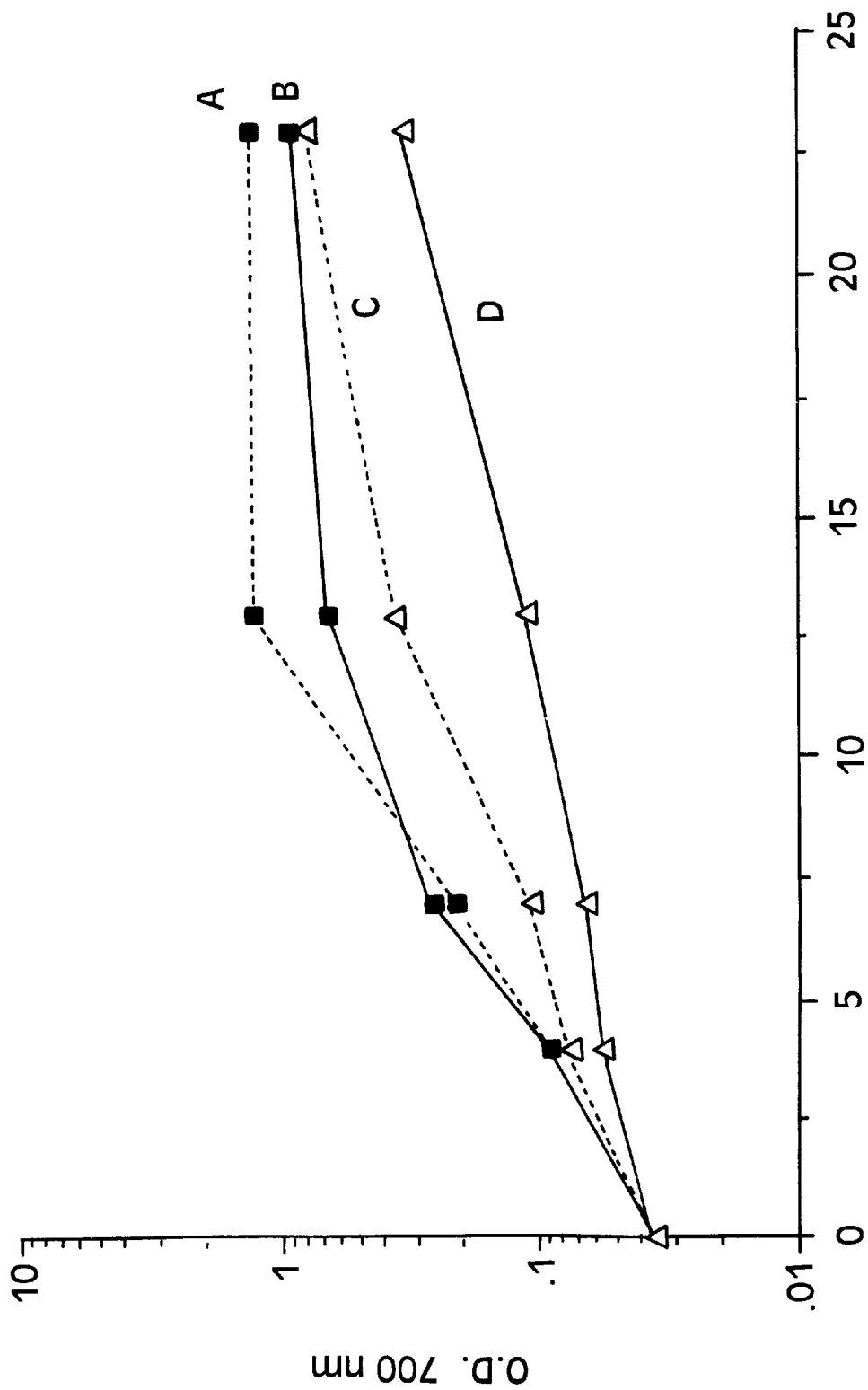
FIG. 5. Growth induction of sodAsodB E. coli with MnTMPyP in minimal media. This figure shows the growth curves in minimal media of E. coli strain AB1157 (black squares) and JI132 (open triangles) in the presence and absence of 24 μM MnTMPyP (dotted lines). Traces are as follows: A) AB1157+24 μM MnTMPyP, B) AB1157 alone, C) JI132+24 μM MnTMPyP, D) JI132 alone. Conditions are as follows: M9 salts in tap water, 0.2w glucose, 0.50 mM each of threonine, leucine, proline, histidine, and arginine, grown at 37° C.

Activity in vivo—SOD-null *E. coli* exhibit several dioxygen-dependent auxotrophies and grow slowly aerobically, whereas they grow as well as the SOD-competent strain under anaerobic conditions (Carlioz et al, EMBO J. 5:623 (1986); Imlay et al, J. Bacteriol. 174:953 (1992)). As shown in FIG. 4, either MnTMPyP or MnTBAP increased the growth of the SOD-null JI132 strain (Imlay et al, J. Bacteriol. 169:2967 (1987)) in a glucose-salts medium supplemented with 0.2% casamino acids. In a simpler medium, the SOD-null grew very slowly under aerobic conditions and, as shown in FIG. 5, MnTMPyP markedly increased this rate of growth. The protection effect of MnTMPyP was also seen when the SOD-null was grown in a manganese-deficient medium buffered with MOPS in place of phosphate.

Several Mn-porphyrins were compared for their abilities to catalyze the dismutation of $O_2^-$ (Table I) and to increase the aerobic growth of the SOD-null strain (Table II). Their order of SOD-like activities in vitro was MnTMPyP>MnTMAP>MnTPyP=MnTMINP=0. In general the SOD-like activities of these complexes assayed in vitro paralleled their activity in vivo with the exception of MnTPyP which was active in vivo although inactive in vitro. FeTMPyP, which was active as a SOD-mimic (Oxygen Radicals in Chemistry and Biology (Bors, W., Saran, M., and Tait, D. Eds) pp. 419–430, Walter de Gruyter, Publ., Berlin (1984)), was toxic at 20 $\mu$M and inhibited the growth of SOD-competent *E. coli*. The metal-free porphyrins caused a slight growth inhibition, as did EDTA, probably by diminishing the availability of essential trace metals.

protective, but to a lesser degree. MnTMPyP was also able to overcome the effect of 5 $\mu$M paraquat on the SOD-null strain. The protective effects of MnTMPyP, so apparent in the amino acid-supplemented glucose plus salts medium, could not be seen in LB medium. This was due to inactivation of the MnTMPyP by a component of the LB medium.

Reduction of MnTMPyP—Centrifugation of *E. coli* (JI132 or AB1157) which had been grown in LB containing 25 $\mu$M MnTMPyP revealed that the cell pellet was red. Since this is the color of the Mn(III) complex, it establishes that the complex is taken into the cells. In contrast, cells grown in the glucose plus salts medium, supplemented with 0.2% casamino acids, were green; while the suspending medium was red. Dithionite converted the Mn(III) TMPyP to a green product, presumably the Mn(II) complex. It thus appears that Mn(III) TMPyP becomes reduced within *E. coli* and that some component of LB medium converts it to a form which cannot be thus reduced.

Figure 7:
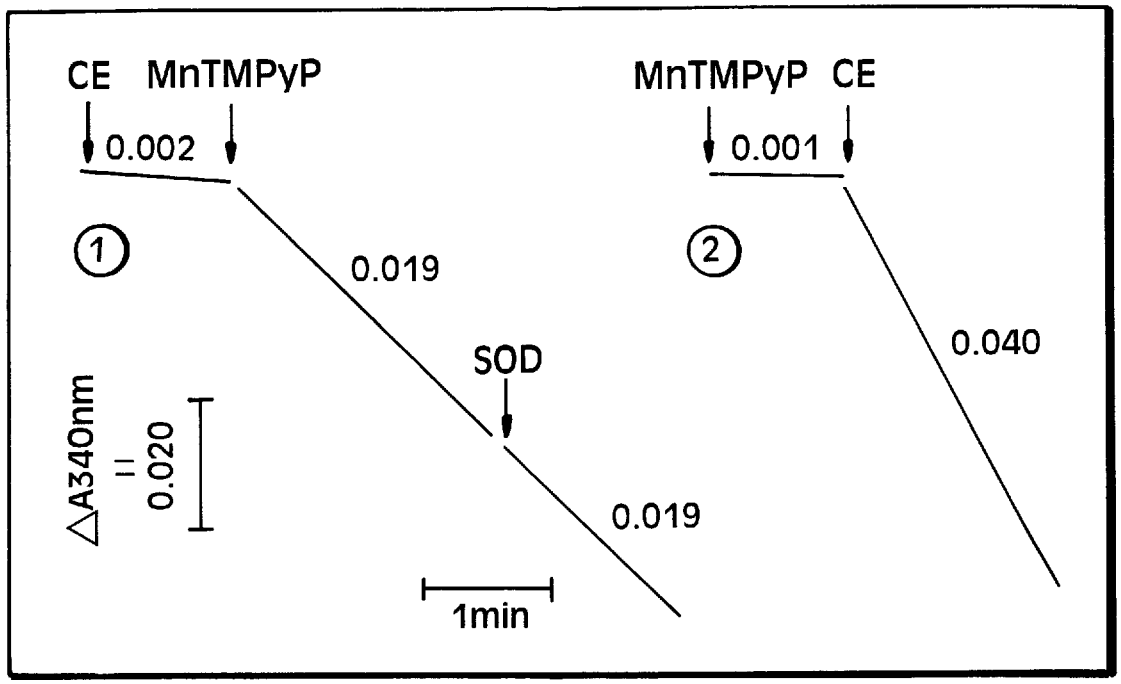
FIG. 7. Effect of MnTMPyP on the oxidation of NADPE by cell extract. Reactions were performed with 0.1 mM NADPH in 50 mM potassium phosphate in 3.0 ml at 25° C. and pH 7.3 and absorbance changes were recorded at 340 nM. Expt. 1—Cell extract (CE) was added to 32 μg protein/ml at the first arrow; MnTMPyP was added to 12.5 μM at the second arrow; and Cu, ZnSOD was added to 50 μg/ml at the third arrow. Expt. 2—MnTMPyP to 25 μM and then cell extract to 32 μg protein/ml—as indicated. Numbers over the lines give the slopes in terms of $\Delta A_{340}$ nm/min.

Anaerobic incubation of 25 $\mu$M TMPyP with cell extract plus 0.1 mM NADPH, in phosphate at pH 7.3 or in Tris at pH 7.8, produced the green color and subsequent aeration restored the original red color. It follows that *E. coli* extract contains an NADPH:Mn(III) TMPyP oxidoreductase. Given that the Mn(II) porphyrin complexes can autoxidize (Oxygen Radicals in Chemistry and Biology (Bors, W., Saran, M., and Tait, D. Eds) pp. 419–430, Walter de Gruyter, Publ., Berlin (1984)), it would be expected that Mn(III) TMPyP should catalytically increase the oxidation of NADPH by extracts of *E. coli*. Trace 1 in FIG. 7 demonstrates that this was the case and that SOD had no effect on this oxidation of NADPH. Mn(III)TMPyP, per se, caused a very slow oxidation of NADPH and this was dramatically increased by cell extract (trace 2). Since 25 $\mu$M Mn(III) TMPyP facilitated the complete oxidation of 100 $\mu$M NADPH by cell extract without any perceptible stable change in the spectrum of the complex; it follows that the complex acted catalytically, being reduced by the NADPH-dependent oxido-reductase and then reoxidized by dioxygen.

TABLE II

Doublinq Times for *E. coli* Strains AB1157 and JI132 in the Presence of Mn Porphyrins

| | | None | CoTMPyP | MnTMPyP | MnTPyP | MnTMAP | MnTBAP |
|---|---|---|---|---|---|---|---|
| | | $t_D$ (min)[a], [concentration of Mn porphyrin] ($\mu$M) | | | | | |
| 2% supplement of casamino acids[b] | AB1157 | 48 | — | 48 [50] | — | — | 48 [50] |
| | JI132 | 240 | 240 [27] | 60 [25] | 90 [19] | 210 [55] | 120 [37] |
| 5 essential amino acids[c] | AB1157 | 130 | 130 [23] | 130 [50] | — | — | — |
| | JI132 | 780 | 780 [23] | 240 [24] | 540 [10] | — | — |

[a] $t_D$ was calculated as the time it takes for the optica density at 700 nm of the sample to double during the log-phase growth period. With the exception of the CoTMPyP growth studies, these results are the average of at least two trials.
[b] Conditions: M9 salts in phosphate buffer, tap water, 0.2% glucose, 2% casamino acids, shaken at 37° C.
[c] Conditions: M9 salts in phosphate buffer, tap water, 0.2% glucose, 0.50 mM each of threonine, leucine, proline, histidine, and arginine, 37° C.

Figure 6:
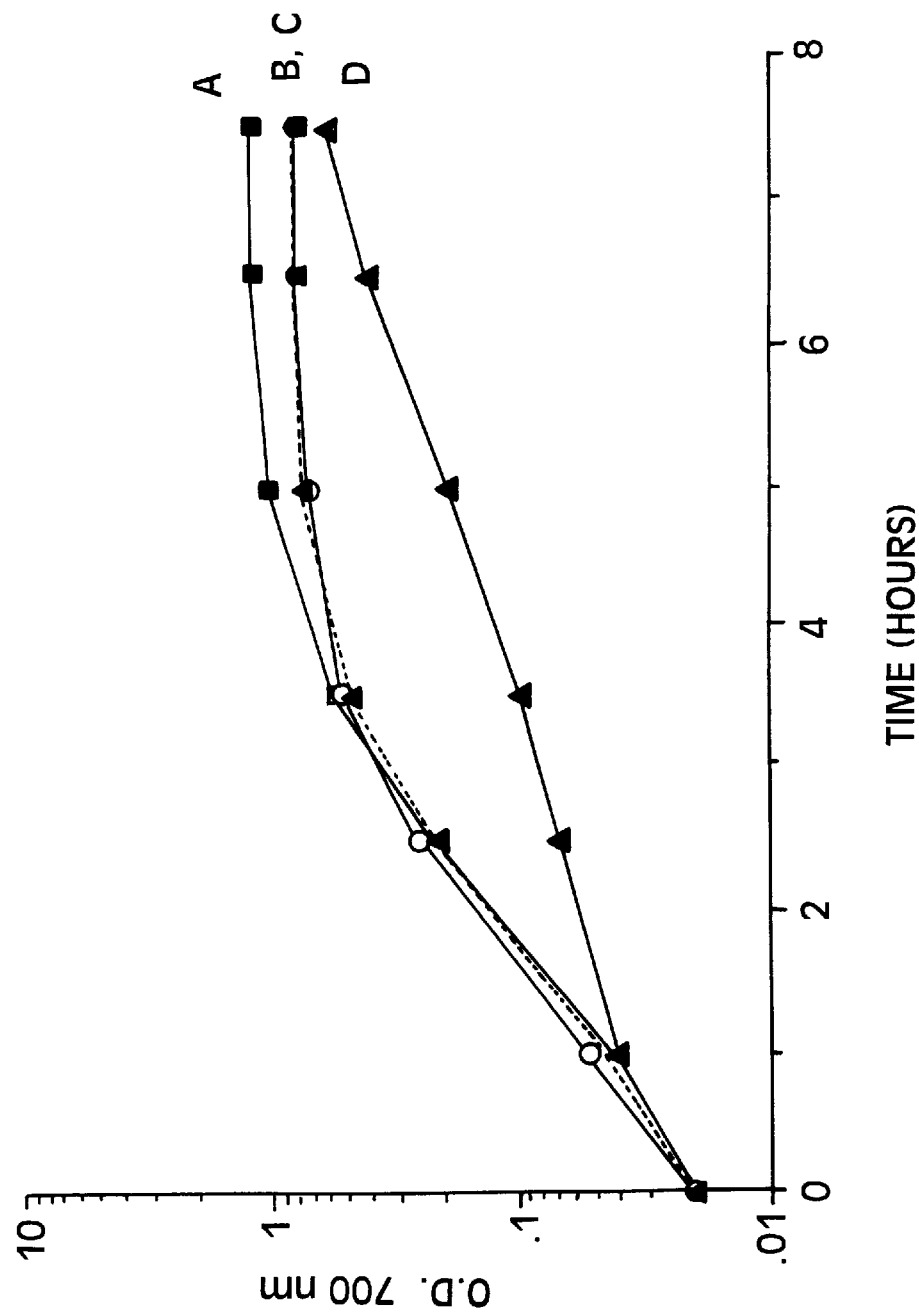
FIG. 6. Protection of E. coli by MnTMPyP against paraquat induced toxicity. This Figure shows the growth curve of the AB1157 strain of E. coli in rich media. Traces are of AB1157 A) alone, B) +20 μM MnTMPyP, C) +10 μM paraquat and 20 μM MnTMPyP, and D) +10 μM paraquat. Conditions are as follows: M9 salts in tap water, 2% casamino acids, 0.2% glucose, 37° C.
Figure 8:
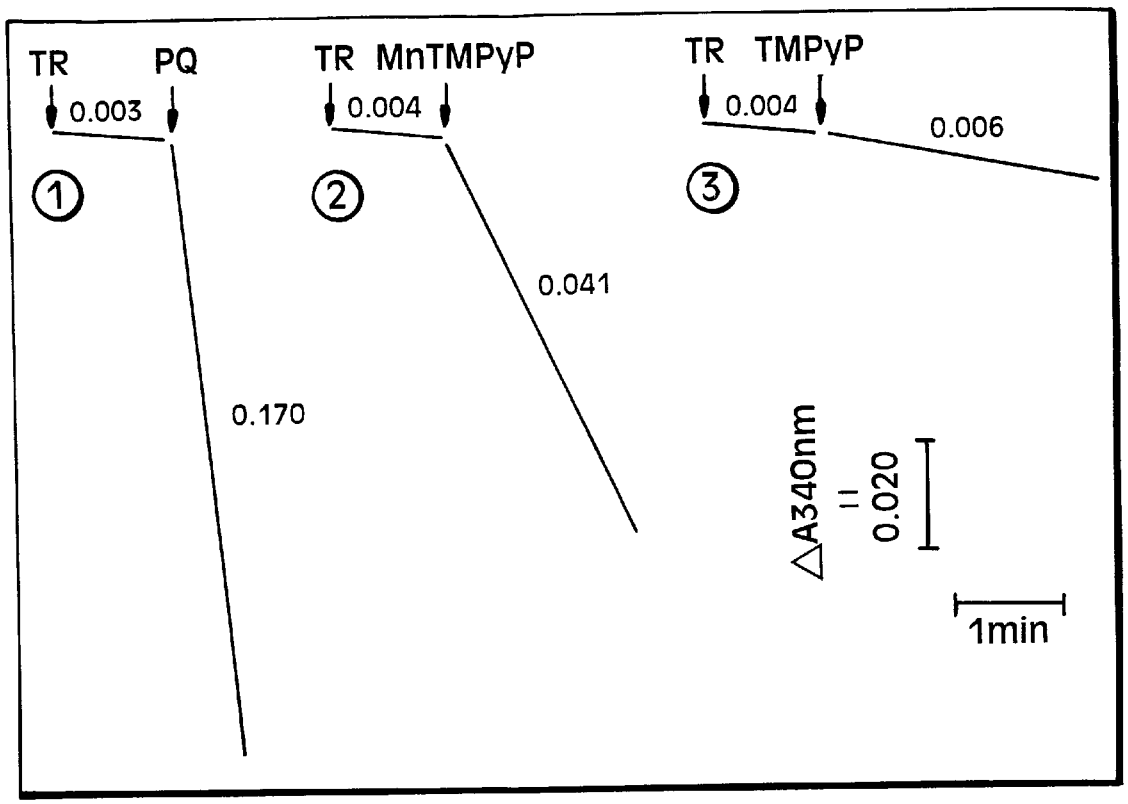
FIG. 8 shows the effect of MnTMPyP on the oxidation of NADPH by thioredoxin reductase. Reaction conditions as in the legend of FIG. 7 except that thioredoxin reductase (TR) was used at 4 μg/ml in place of cell extract. In expt. 1, paraquat (PQ), where indicated, was added to 4.0 mM, in experiment 2, MnTMPyP was added to 25 μM, and, in expt. 3, the metal-free porphyrin was used in place of MnTMPyP.

Mn(II), per se, at 2 or 95 $\mu$M, did not perceptibly overcome the growth-inhibiting effect of 30 $\mu$M paraquat. In contrast, 20 $\mu$M MnTMPyP eliminated, virtually completely, the growth inhibition imposed upon AB1157 (Imlay et al, J. Bacteriol. 174:953 (1992)) by 10 $\mu$M paraquat (FIG. 6). Furthermore, 25 $\mu$M MnTMPyP was found to eliminate the growth inhibitory effect of 20 $\mu$M paraquat and to partially alleviate the growth inhibition caused by 40 $\mu$M paraquat on the SOD-competent strain. MnTPyP was similarly Thioredoxin reductase was able to substitute for cell extract in these measurements. Trace 1 in FIG. 8 shows that paraquat strongly stimulated the oxidation of NADPH by thioredoxin reductase, while trace 2 demonstrates that MnTMPyP was also active while the porphyrin without the manganese was not significantly active (trace 3). Under anaerobic conditions, the MnTMPyP was converted to the green reduced form by thioredoxin reductase plus NADPH. Several other complexes were examined. MnTPyP caused a slow oxidation of NADPH and this was markedly increased by thioredoxin reductase. In contrast, Co(II)TMPyP and Fe(III)TMAP rapidly and non-enzymically oxidized NADPH.

Figure 9:
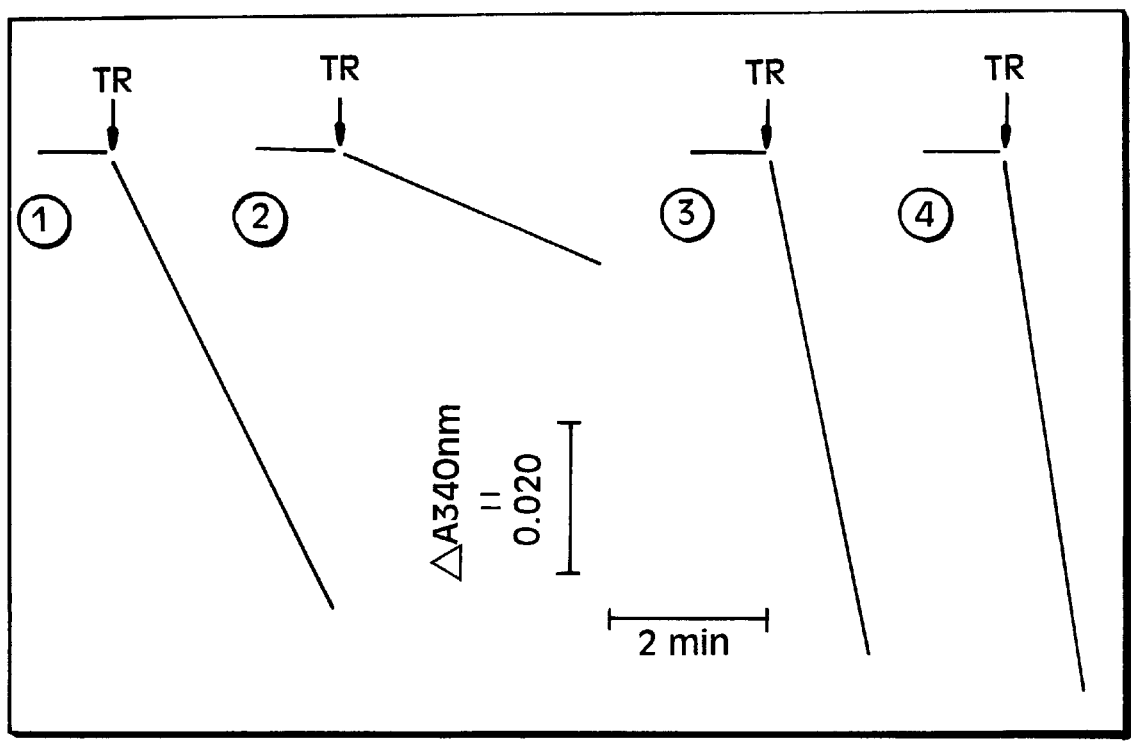
FIG. 9. LB medium blunts the ability of MnTMPyP to stimulate NADPH oxidation by thioredoxin reductase. Reaction mixtures of 3.0 ml contained 0.1 mM NADPH and additional components in 50 mM potassium phosphate buffer at pH 7.3 and at 25° C. Expt. 1–25 μM MnTMPyP present at outset and thioredoxin reductase (TR) added to 2.0 μg/ml at the arrow. Expt. 2—as in Expt. 1 except that 20% of the phosphate buffer was replaced by LB medium. Expt. 3–4.0 mM PQ present at the outset and TR added to 0.67 μg/ml at the arrow. Expt. 4—as in expt. 3 except that 20% of the phosphate buffer was replaced by LB medium.

Effect of LB Medium—The observation that LB medium elminiated both the protection by, and the greening effect of, MnTMPyP: suggested that some component of this complex medium was intefering with reduction of this complex. Traces 1 and 2 in FIG. 9 show that 20% LB in the reaction mixture inhibited the oxidation of NADPH by cell extract plus MnTMPyP; whereas it had no effect when paraquat was used in place of the Mn-porphyrin (traces 3 and 4). It seems likely that some component of the LB medium, very likely some component of the yeast extract, converts the Mn(III) TMPyP to a form which is not easily reduced by NADPH:Mn(III)TMPyP oxidoreductases, such as thioredoxin reductase.

Figure 10:
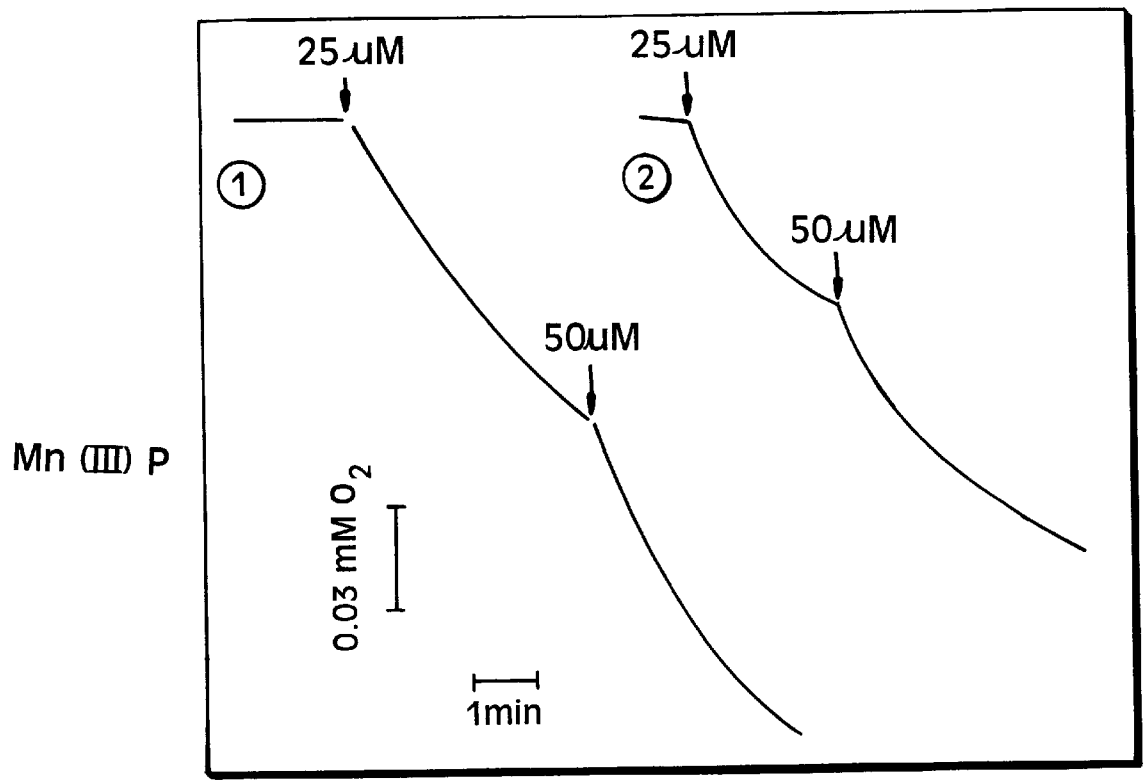
FIG. 10. Oxidation of GSH catalyzed by MnTMPyP. Reaction mixtures contained 10 mM GSH in 50 mM buffer at the arrows. MnTMPyP was added to 25 μM or to an additional 50 μM, as indicated and $O_2$ uptake was monitored. Expt. 1 in phosphate at pH 7.3 and expt. 2 in Tris-HCl at pH 7.8.
Figure 11:
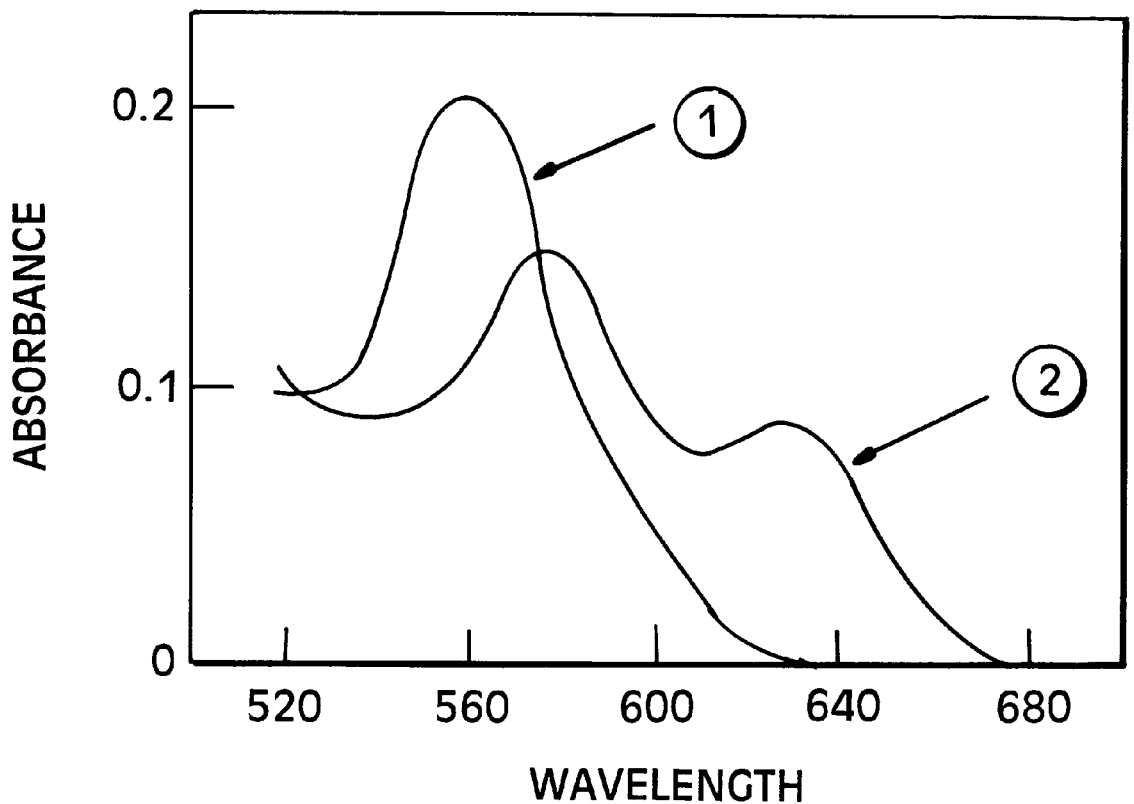
FIG. 11. Optical absorption spectra of MnTMPyP. The MnTMPyP was at 25 μM in 50 mM Tris-HCl at pH 7.8 and at 25° C. Spectrum 1—anaerobic; spectrum 2—anaerobic plus 5 mM GSH, recorded 5 minutes after mixing.

Non-Enzymic Reduction of Mn (III) TMPyP—The red Mn(III) porphyrin was converted to the green form by incubation with 2–10 mM GSH in phosphate at pH 7.3 or in Tris at pH 7.8. If the green form is indeed the autoxidizable Mn(II)TMPyP then Mn(III)TMPyP should catalyze the oxidation of GSH. Trace 1 in FIG. 10 shows that addition of 25 $\mu$M Mn(III)TMPyP to 10 mM GSH in phosphate at pH 7.3 caused an oxygen consumption the rate of which decreased during several minutes of observation. Subsequent addition of additional Mn(III)TMPyP reinstated the more rapid $O_2$ consumption. Trace 2 records similar effects in Tris at pH 7.8. It appears that Mn(III)TMPyP does catalyze the oxidation of GSH but that it is gradually inactivated during incubation with GSH. The effect of anaerobic incubation with GSH upon the long wavelength absorption spectrum of MnTMPyP is shown in FIG. 11. This change in spectrum was also caused by anaerobic incubation of the compound with dithionite, or with NADPH in the presence of thioredoxin reductase, or cell extract.

All documents cited above are hereby incorporated in their entirety by reference.

One skilled in the art will appreciate from a reading of this disclosure that various changes in form and detail can be made without departing from the true scope of the invention. One skilled in the art will appreciate from a reading of this disclosure that Mn-porphyrins are not the only compounds that function as oxidoreductases. Riley & Weiss have described a Mn(II)penta-azacyclopentadecane that catalyzes the dismutation of $O_2^-$ with a rate constant $4 \times 10^7$ $M^{-1}s^{-1}$ (Riley et al, J. Am. Chem. Soc. 116:387 (1994)). Since the Mn(III) form of this compound is a potent oxidant, in vivo reaction is likely due to NADPH and GSH, rather than to $O_2^-$.

What is claimed is:

1. A method of effecting oxidoreduction in a patient comprising administering to said patient a metallic porphyrin complex having substituents on the methine carbons of the porphyrin, in an effective, nontoxic amount, so that said complex is reduced by a reductant present in said patient and reoxidized by $O_2^-$ present in said patient.

2. The method according to claim 1 wherein said substituents on said methine carbons are such that said metallic porphyrin complex, in vivo, has superoxide dismutase activity.

3. The method according to claim 2 wherein said substituents comprise a pyridyl or phenyl group.

4. The method according to claim 1 wherein said metal complex protects a superoxide dismutase (SOD) competent strain of E. coli against paraquat.

5. The method according to claim 1 wherein said metal complex protects a SOD-null strain of E. coli against dissolved oxygen.

6. The method of claim 1 wherein said metal or manganese, iron, copper, cobalt or nickle.

7. The method of claim 6 wherein said metal is manganese.

8. The method according to claim 1 wherein said reductant is NADH or NADPH.

9. The method according to claim 1 wherein said reductant is GSH.

10. The method according to claim 1 wherein said substitutents on said methine carbons are the same.

11. The method according to claim 10 wherein each of said methine carbons bears a substituent.

12. The method according according to claim 10 wherein said metal is manganese, iron, copper, cobalt or nickle.

13. The method according to claim 12 wherien said metal is manganese.

14. The method according to claim 10 wherein said reductant is NADH or NADPH.

15. The method according to claim 10 wherein said reductant is GSH.

16. The method according to claim 11 wherein said metal is manganese, iron, copper, cobalt or nickle.

17. The method according to claim 16 wherein said metal is manganese.

18. The method according to claim 11 wherein said reductant is NADH or NADPH.

19. The method according to claim 11 wherein said reductant is GHS.

* * * * *